United States Patent [19]

Smith et al.

[11] B 4,000,211

[45] Dec. 28, 1976

[54] DIMERIZATION OF MONOOLEFINS WITH CATALYSTS ON SOLID SUPPORTS

[75] Inventors: Clifford E. Smith; Edward L. Czenkusch; Grant C. Bailey, all of Bartlesville, Okla.

[73] Assignee: Phillips Petroleum Company, Bartlesville, Okla.

[22] Filed: Dec. 26, 1973

[21] Appl. No.: 428,103

[44] Published under the second Trial Voluntary Protest Program on February 10, 1976 as document No. B 428,103.

Related U.S. Application Data

[63] Continuation of Ser. No. 872,409, Oct. 29, 1969, abandoned.

[52] U.S. Cl. .................. 260/683.15 D; 252/430
[51] Int. Cl.$^2$ ............................ C07C 3/21
[58] Field of Search .............. 260/683.15 D

[56] References Cited

UNITED STATES PATENTS

| | | | |
|---|---|---|---|
| 3,482,001 | 12/1969 | Eberhardt | 260/683.15 D |
| 3,483,269 | 12/1969 | Magoon et al. | 260/683.15 D |
| 3,591,656 | 7/1971 | Kroll | 260/683.9 |
| 3,592,869 | 7/1971 | Cannell | 260/683.15 D |
| 3,709,953 | 1/1973 | Bergem et al. | 260/683.15 D |
| 3,755,490 | 8/1973 | Yoo et al. | 260/683.15 D |

FOREIGN PATENTS OR APPLICATIONS

| | | |
|---|---|---|
| 711,042 | 8/1968 | Belgium |

*Primary Examiner*—Paul M. Coughlan, Jr.

[57] ABSTRACT

Ethylene and/or propylene is dimerized by contacting the monoolefin with a catalyst formed by depositing a nickel complex such as bis(3-picoline)dichloronickel or bis(tributylphosphine)dichloronickel on a solid support such as silica-alumina. Preferably, an aluminum compound such as diethylaluminum chloride is also used in preparing the catalyst.

16 Claims, No Drawings

DIMERIZATION OF MONOOLEFINS WITH CATALYSTS ON SOLID SUPPORTS

This is a continuation of copending application Ser. No. 872,409, filed Oct. 29, 1969, now abandoned.

This invention relates to the dimerization of monoolefins. In another aspect, this invention relates to the dimerization of monoolefins with catalysts comprising nickel compounds deposited on solid supports.

The dimerization of the lower monoolefins using homogeneous catalyst systems comprising a transition metal complex and an aluminum compound is known in the art. The process of this invention is an improvement in the prior art process, i.e. a number of advantages are obtained by distributing such a catalyst system over a selected solid support.

Accordingly, it has been discovered that lower monoolefins can be dimerized by contacting under reaction conditions at least one monoolefin with a catalyst formed by depositing a nickel complex such as bis(3-picoline)dichloronickel or bis(tributylphosphine)dichloronickel on a solid support such as silica or silica-alumina, preferably also adding an aluminum compound such as diethylaluminum chloride.

An object of this invention is to provide a process for the dimerization of lower monoolefins.

Another object of this invention is to provide a process for the dimerization of lower monoolefins with a catalyst employing a solid support material.

Other objects, advantages, and features of this invention will be apparent to one skilled in the art from the disclosure and claims.

The monoolefins that can be employed in this invention are ethylene and propylene.

The nickel complexes employed in the preparation of the catalyst system of this invention are well known in the art. These nickel complexes include all hydrocarbon-soluble organo complexes of nickel. The nickel in such complexes can be divalent, monovalent or zero valent. Preferably, these nickel complexes have the formula:

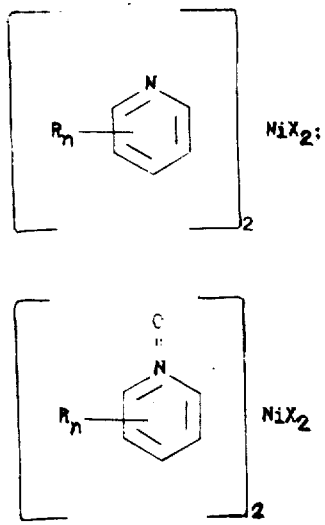

or $(R_3Q)_2NiX_2$, wherein R is an alkyl, alkenyl, cycloalkyl, or aryl radical or a combination thereof having up to 20 carbon atoms; n is zero or an integer from 1 to 5; each X is chlorine, bromine, iodine or fluorine; preferably chlorine; and Q is phosphorus, arsenic, or antimony, preferably phosphorus.

Specific examples of suitable nickel complexes are:
bis(tri-n-butylphosphine)dichloronickel,
bis(triphenylphosphine)dichloronickel,
bis(pyridine)dichloronickel,
bis(triphenylphosphine oxide)dibromonickel,
bis(triphenylarsine oxide)dibromonickel,
bis(3-picoline)diiodonickel,
bis(4-picoline)diiodonickel,
bis(4-ethylpyridine)difluoronickel,
bis(2,4-pentanedionato)nickel,
bis(cyclopentadienyl)nickel,
bis($\pi$-allyl)iodonickel,
triphenylphosphine($\pi$-allyl)iodonickel,
bis(tribenzylarsine)dibromonickel,
bis(tri-o-xylylstibine)diiodonickel,
bis(trieicosylphosphine)diacetatonickel,
bis(triphenylphosphine)nitrosyliodonickel,
bis(N,N-di-n-butyldithiocarbamato)nickel,
bis(N,N-dimethyl-$\beta$-mercaptoethylamine)nickel,
bis(2-picoline-N-oxide)dinitratonickel,
bis[N,N-dicyclohexyl-2-(cyclohexylamino)-malonamide]dichloronickel,
bis(diphenylchlorophosphine)2,4-pentadieneonylnickel,
bis(tricyclohexylphosphineoxide)dibromonickel,
bis(N-tridecyl-$\beta$-mercaptoethylamine)nickel, and the complex nickel salts of:
2-hydroxy-4,4'-didodecylbenzophenone,
2-hydroxy-4-methylbenzophenone,
3,4-di-t-butylsalicyladehyde,
o,o'-thiobis(p-1,1,3,3-tetramethylbutylbenzophenone),
N-salciylidene-4-methylcyclohexylamine,
and the like and mixtures thereof.

The aluminum compound of the catalyst system of this invention is represented by the formula $R_xAlX_y$, wherein R and X are as previously defined, x and y are 0 or integers from 1 to 3 whose sum is 3.

Some examples of the aluminum compound are methylaluminum dichloride, dimethylaluminum chloride, diethylaluminum bromide, ethylaluminum dibromide, aluminum trichloride, triethylaluminum, vinylaluminum diiodide, dibutylaluminum chloride, aluminum tribromide, phenylaluminum dibromide, triisobutylaluminum, dibenzoaluminum dichloride, 4-tolylaluminum dichloride, cyclohexylaluminum fluoride, dodecylaluminum dibromide, eicosylaluminum dichloride, butylaluminum dichloride, and mixtures thereof including methylaluminum sesquichloride, ethylaluminum sesquichloride, and the like. The preferred aluminum compounds are organoaluminum halides, particularly where the organic radical is a lower alkyl group and the halogen is chlorine. Particularly effective results are obtained with diethylaluminum chloride.

When an aluminum compound is employed in the catalyst system, the mole ratio of aluminum compound to nickel is in the range from 0.5:1 to 20:1, preferably from 1:1 to 10:1, and still more preferably from about 2:1 to about 6:1.

The solid supports that can be employed in this invention are, generally, the difficult-to-reduce metal oxides which are of catalytic grade and which, when slurried with distilled and decarbonated water exhibit a pH below 6 and preferably below 4. By catalytic grade it is meant that the supported materials should have a surface area of at least 50 and preferably at least 100 square meters per gram. These supports can contain minor amounts of other metal oxides, but they must remain acidic as previously stated. Therefore, supports such as silica or alumina which contain sufficient alkali metal oxides so as to produce a slurry with a pH greater than 6 will not be suitable for the process of this invention.

Specific examples of suitable solid supports are silica, alumina, silica-alumina, titania, boria, zirconia, and the like, and mixtures thereof.

The solid supports should be conventionally heat-treated before forming the catalyst composition. Calcination in flowing air at 800°–1500° F. for 0.1 to 24 hours is generally suitable. The support material can be in any convenient form such as a powder, agglomerates, granules, pellets, or the like.

The catalyst system of this invention can be formed by combining the nickel complex, the aluminum compound, and the solid support in a number of different ways. One method is to pass a hydrocarbon solution of the nickel complex through a bed of the heat-treated support such that the nickel complex is adsorbed onto this solid. With or without evaporation of the residual solvent, a hydrocarbon solution of the suitable aluminum compound can then be passed over the bed of support such that the aluminum compound is also adsorbed on the solid. The order of contacting can be reversed, if desired, but it is presently preferred to contact the solid with a nickel complex first. Still another way is to form the complex in situ on the solid support material. Thus, the bed of the pre-activated solid support can be treated first with a relatively simple nickel compound such as nickel acetylacetonate and then with suitable complexing agents of a type to form the desired nickel complex. Finally, the aluminum compound can be applied.

Still another way is to separately meter each of the three components, namely, the nickel complex, the aluminum compound, and the solid support, into the reaction zone such that the total solid catalyst composition is formed in situ. Still another method of forming the catalyst system is to add the nickel complex and the aluminum compound to the solid support in the presence of a suitable diluent such that a slurry is formed. This slurry then can be conveniently pumped into the reaction zone of a batch or continuous process.

In still another method, a slurry can be made from the solid support, the nickel complex, and a suitable solvent. This slurry then is pumped into the reaction zone and contacted with the monoolefin before the addition of the organoaluminum compound as it is sometimes desirable for the nickel complex to be contacted with the monoolefin before contact with the organoaluminum compound.

The solid supports of this invention have been found to have an affinity for the nickel complex and the aluminum compounds of the catalyst system. Consequently, the proportion of nickel complex to the solid support is not greater than that which the solid support can conveniently adsorb. This maximum level varies depending upon the specific support and the specific nickel complex utilized but can be readily determined by simple experimentation. One method of determining this is to pass a solution of the nickel complex through a bed of the solid support until no more of the nickel complex is adsorbed. The quantity of nickel complex contained on the solid, determined by conventional analytical techniques, is thus the saturated or maximum level of nickel complex for that specific system. Once such a maximum level has been determined, the nickel complex and the solid support can be combined more simply by any of the preceding methods of preparing the catalysts.

Ordinarily, it is preferred that solid not be saturated with a nickel complex or the aluminum compound but only from about 10 to about 90 percent of the amount sufficient to saturate the solid is ordinarily used. To illustrate this, a particulate catalyst grade silica was found to adsorb a maximum of about 6.35 weight percent of bis(tri-n-butylphosphine)dichloronickel based upon the weight of the support. Subsequently, only a quantity of the nickel complex amounting to about 5 weight percent based on the solid was used in the preparation of the solid catalyst.

The monoolefin dimerization process of this invention can be carried out using a number of conventional contactinig techniques. The solid catalyst system can be used as a mobile catalyst system either in the presence of a suitable diluent — a slurry operation — or in the absence of any diluent and in the gas phase — a fluidized catalyst bed operation. Such modes of reaction are conventional and can be carried out either continuously or batchwise. In the slurry form of operation, suitable solvents are inert materials such as paraffinic or aromatic hydrocarbons and their halogenated derivatives. In some instances, a portion of the dimer product can be recycled to the reaction zone to act as the diluent.

If desired, the supported catalyst system of the present invention can be formed into a fixed catalytic bed through which the feed olefin can be passed either with or without a diluent. The preferred mode of operation, however, is the slurry form of operation.

Because the dimerization is highly exothermic, heat must be removed from the process. With the slurry form of operation, for example, the reaction zone can be jacketed to provide heat exchange with a coolant or the reactor may be operated under boiling conditions such that the volatized fraction is cooled and refluxed back into the reaction zone in such a manner so as to remove the heat from the reaction zone and act as a means for controlling the reaction temperature.

The dimerization of the monoolefin can take place at temperatures within the range of $-50°$ to $225°$ F., and preferably within the range of $32°-150°$ F. Normally, it is desirable to carry out the dimerization reaction under pressures ranging up to about 2000 psig and preferably 20 to 500 psig. The time of contact of the monoolefin with the catalyst for the dimerization varies depending upon the desired degree of conversion but generally is within the range of about 0.1 minutes to about 20 hours, preferably 5 to 120 minutes. The proportion of the catalyst composition to the olefin feed in the reaction zone generally is within the range of about 0.00001 to about 0.1 moles of nickel complex per mole of olefin feed.

It has been found that the supported catalyst system of this invention can operate at somewhat higher temperatures and still obtain results equivalent to those produced by the non-supported homogeneous process counterpart. In general, however, higher temperatures sometimes tend to produce greater quantities of the heavier, more highly polymerized particles. Consequently, the lowest reaction temperatures which can provide the desired degree of conversion and the desired selectivity to the products is ordinarily used.

At the completion of the reaction, or after removing the effluent from the reaction zone, the catalyst system of the present invention can be removed from the product by simple filtration or decantation. Essentially all of the nickel complex and all of the aluminum compound can thus be removed.

One advantage of this invention is that a homogeneous catalyst can be converted into a heterogeneous catalyst system which can then be handled as a solid and hence, more easily removed from the reactor effluent. Another advantage is that the supported catalyst system, which is now in the form of particulate solid, can be used in a fluidized bed mode of operation for the dimerization of monoolefins. Still further, the use of the supported catalyst system of this invention is very effective in reducing or essentially eliminating the down time encountered with processes employing the homogeneous catalyst systems. It has been found that such processes employing the homogeneous catalyst systems suffer from a buildup of deposits upon the reactor walls particularly upon these surfaces which are used as heat exchange sufaces to cool the reaction mixture. These deposits are complex and contain highly polymerized material, which, though a very minor product of the reaction, can accumulate over a period of time. Such deposits have also been found to contain residues from the spent catalyst. It has now been found that these deposits can be substantially reduced if not eliminated by the present invention because such residues build up not on the reactor or heat exchanger walls but are retained on the relatively extensive surface provided by the solid catalyst system.

The advantages of this invention are further illustrated by the followiwng examples. The reactants and the proportions and other specific conditions are presented as being typical and should not be construed to limit the invention unduly.

EXAMPLE I

A 2 ml (0.8190 gram) quantity of granular silica-alumina (containing 13 weight percent alumina) was charged into a vertically-positioned reactor which was about 10 cm long, had an ID of 8 mm, and had a fritted glass support plate at the bottom. The silica-alumina had been pre-activated by heating over night in flowing dry air at 1000° F. It had then been purged with nitrogen and cooled. The bed was impregnated with 26.2 ml of 0.01 molar solution of bis(tri-n-butylphosphine)dichloronickel and then washed with 5 ml of pentane. The nickel complex-containing bed was then further contacted with 3.3 ml of 1.704 molar solution of triethylaluminum in n-hexane and then washed with another 5 ml of pentane. The catalyst bed was then dried by a stream of dry nitrogen.

A stream of ethylene at a gaseous hourly space velocity of about 1000 was then passed through the reactor and maintained at about 300° F. and at atmospheric pressure. The ethylene flow maintained a fluidized catalyst condition during the run which was allowed to continue for 1.5 hours.

The results of the reaction during this period are shown in Table I which also contains the results of several other runs carried out under essentially identical conditions except that the aluminum compound and solid support material were varied. The Al:Ni ratio was 10 in each run.

TABLE I

| Run No. | Aluminum[a] Compound | Support | Run Time, Hr. | Conv. % | Selectivity to Butenes | Butene Distribution | |
|---|---|---|---|---|---|---|---|
| | | | | | | 1-Butene | 2-Butene |
| 1 | DEAC | Silica-alumina | 2 | 73 | 68 | 12 | 88 |
| 2 | EADC | same | 1.5 | 46 | 60 | 14 | 86 |
| 3 | TEA | same | 1.5 | 19 | 56 | 70 | 30 |
| 4 | DEAC | Cab-O-Sil[b] | 3 | 69 | 68 | 15 | 85 |
| 5 | EADC | " | 1.5 | 32 | 67 | 34 | 66 |

[a]DEAC - diethylaluminum chloride
EADC - ethylaluminum dichloride
TEA - triethylaluminum
[b]A commercial finely divided, non-porous, flame hydrolyzed silica.

The data in the table above show that the solid catalyst of the present invention can employ several different aluminum compounds and several different solid support materials. Moreover, it is seen that such a catalyst system is suitable for use in a solventless fluidized bed process to dimerize ethylene.

EXAMPLE II

A 2 ml (0.9140 g) quantity of the same preactivated silica-alumina described in Example I was impregnated with 11.6 ml of 0.01 molar solution of bis(tri-n-butylphosphine)dichloronickel in pentane. The volatiles were evaporated and the impregnating granular solid was transferred to a reactor with 225 g of pentane. The reactor was flushed with ethylene and 0.7 ml of a 0.865 molar solution of diethylaluminum chloride in pentane was added. Ethylene was then pressured into the reactor at about 60 psig and the reaction was allowed to continue for 1 hour at 75° F. with stirring.

Analysis of the reaction mixture showed that butenes were produced at the rate of 10,500 grams butenes per gram nickel complex per hour and at a selectivity of 90.5 percent.

Other similar runs were carried out at slightly different conditions as shown in Table II. The Al:Ni ratio in each run was 10.

TABLE II

| Run No. | Reaction Time | Catalyst Wt., g | Press. psig | Temp. °F | Selectivity to Butenes | Productivity g/g Ni Complex |
|---|---|---|---|---|---|---|
| 1 | 1 | 1.17 | 50 | 40 | 97.0 | 2,670 |
| 2 | 2 | | 68 | 40 | 95.4 | 2,960 |
| 3 | 3 | | 224 | 40 | 96.1 | 1,260 |

TABLE II-continued

| Run No. | Reaction Time | Catalyst Wt., g | Press. psig | Temp. °F | Selectivity to Butenes | Productivity g/g Ni Complex |
| --- | --- | --- | --- | --- | --- | --- |
| 4 | 4 | | 316 | 40 | 96.5 | 135 |
| 5 | 1 | 1.10 | 58 | 100 | 89.3 | 4,390 |
| 6 | 2 | | 63 | 100 | 90.8 | 7,780 |
| 7 | 3 | | 72 | 100 | 87.0 | 6,290 |
| 8 | 2.5 | 0.12 | 150 | 88 | 95.9 | 7,293 |
| 9[1] | 1 | 0.91 | 60 | 75 | 90.5 | 10,500 |
| 10 | 5.0 | 0.17 | 160 | 85–90 | 95.3 | 34,351 |
| 11 | 2.5 | 0.37 | 150 | 160 | 80.1 | 12,391 |

[1]DEAC added to reactor. In other runs, DEAC deposited on catalyst.

The data in the table above show that the catalyst of the present invention can be used with effectiveness under varying conditions in a stirred catalyst slurry system for the dimerization of ethylene.

EXAMPLE III

The dimerization of propylene was carried out in a fluidized operation similar to the run shown in Example I using the same catalyst, reactor, and space rate. Propylene was also dimerized using the catalyst slurry method of Example II. The results are shown in Table III.

TABLE III

| Run No. | Run Time Hr. | Temp. °F | Conv. % | % Selectivity to Hexenes | Distribution of $C_6$ Isomeric Structures[3] | | |
| --- | --- | --- | --- | --- | --- | --- | --- |
| | | | | | 2,3-Dimethyl-butane | 2-Methyl-Pentane | n-Hexane |
| 1 | 3.0 | 100 | 8.2 | 94 | 24.4 | 63.0 | 12.0 |
| 2[1] | 3.0 | 85 | 3062[2] | 94 | 25 | 65 | 10 |

[1]Carried out batch using catalyst slurry method. 100 g propylene and 2 ml catalyst. (Run 1 used fluidized method.)
[2]Productivity: g hexenes/g Ni complex
[3]Determined on hydrogenated sample.

These data show that the invention catalyst and process are also very effective for the dimerization of propylene.

EXAMPLE IV

The ethylene dimerization runs of this example were carried out in a manner similar to Example II. Reaction pressure was 300 psig and the temperature was varied as indicated in Table IV. Bis(tri-n-butylphosphine)-dichloronickel, diethylaluminum chloride and silica-alumina support were employed in the dimerization of ethylene. The results are shown in Table IV.

TABLE IV

| Temp. °F | Reaction Time Hours | Wt. % Selec. to Butenes | Al/Ni Ratio | Productivity, grams of butene/ gram of Ni Complex |
| --- | --- | --- | --- | --- |
| 212 | 0.5 | 81 | 10:1 | 1510 |
| 212 | 1.0 | 70 | 6:1 | 2950 |
| 160 | 2.0 | 86 | 6:1 | 9980 |
| 130 | 5.0 | 91 | 6:1 | 8240 |
| 100 | 1.0 | 94 | 6:1 | 13430 |
| 212 | 1.0 | 53 | 2:1 | 6050 |
| 160 | 3.0 | 92 | 2:1 | 15400 |
| 130 | 2.0 | 91 | 2:1 | 22050 |

TABLE IV-continued

| Temp. °F | Reaction Time Hours | Wt. % Selec. to Butenes | Al/Ni Ratio | Productivity, grams of butene/ gram of Ni Complex |
| --- | --- | --- | --- | --- |
| 130 | 6.6 | 91 | 1:1 | 3275 |

These runs demonstrate the effect of temperature and Al/Ni ratio on the productivity and selectivity of ethylene dimerization with supported nickel complexes.

EXAMPLE V

These runs were carried out in a manner identical to Example IV except that no aluminum compound was employed. The results are given in Table V.

TABLE V

| Temp. °F | Reaction Time Hours | Al/Ni Ratio | Wt. % Selec. to Butenes | Productivity grams of butene/ gram of Ni complex |
| --- | --- | --- | --- | --- |
| 212 | 0.5 | 0 | 94 | 630 |
| 160 | 1.0 | 0 | 94 | 2150 |
| 130 | 1.5 | 0 | 93 | 6890 |

These runs demonstrate that the monoolefins of this invention can be dimerized with nickel complexes on solid silica-alumina supports without the presence of an aluminum compound.

EXAMPLE VI

The runs of this example were similar to the runs of Example IV. The reaction pressure was 300 psig and the reaction temperature was 130° F. The results are given in Table VI.

TABLE VI

| Support Material | pH Support Water Slurry | Surface Area of Support $m^2/g$ | Wt. Nickel Complex g. | Ratio Al/Ni | Wt. Total Catalyst g. | Time Hrs. | Productivity g/g Ni Complex | Selectivity to Butenes % |
| --- | --- | --- | --- | --- | --- | --- | --- | --- |
| Synthetic Zeolite[1] | 9.2 | — | 0.00785 | 2 | 0.5189 | 0.75 | 53 | 34 |
| Charcoal | 11.3 | 870 | 0.0591 | 6 | 1.1028 | 2.6 | 625 | 96 |

TABLE VI-continued

| Support Material | pH Support Water Slurry | Surface Area of Support m²/g | Wt. Nickel Complex g. | Ratio Al/Ni | Wt. Total Catalyst g. | Time Hrs. | Productivity g/g Ni Complex | Selectivity to Butenes % |
|---|---|---|---|---|---|---|---|---|
| Silica Gel[2] | 6.6 | 240 | 0.0267 | 2 | 0.4682 | 1.8 | 1870 | 93 |
| Silica Gel[2], Treated[3] | 2.66 | — | 0.0143 | 6 | 0.7519 | 1.58 | 4300 | 86 |
| Silica Gel[4] | 3.3 | 717 | 0.00619 | 6 | 0.1366 | 1.12 | 50900 | 90 |
| Silica Gel[4], Treated[3] | 3.05 | — | 0.0093 | 6 | 0.2008 | 2.8 | 23000 | 93 |
| Silica-Alumina[5] | 3.95 | 600 | 0.0090 | 2 | 0.1600 | 2.0 | 22050 | 91 |
| Silica-Alumina[5], Treated[6] | 3.90 | — | 0.0144 | 6 | 0.2689 | 2.53 | 17400 | 90 |
| Silica-Magnesia | 8.4 | — | 0.1021 | 6 | 1.9018 | 2.0 | 870 | 90 |

[1]SK-45 Mol sieve, commercial silica and alumina-containing adsorbent.
[2]Commercial microspheroidal, intermediate density silica gel.
[3]Treated three times with hot ammonium acetate solution, then 1 weight % $H_2SO_4$ added as $(NH_4)_2SO_4$ before calcination.
[4]Commercial microspheroidal silica gel.
[5]Same as in Example 1.
[6]1 Weight % $H_2SO_4$ added as $(NH_4)_2SO_4$ before calcination.

The data in Table VI illustrate that, for best results, the acidity of the support material is critical. Those solid catalyst support materials which have a pH (when slurried in distilled and decarbonated water) of less than about 6 are very effective. Acidic treatment of the supports with acidic reagents result in little or no improvement.

EXAMPLE VII

Additional runs were conducted in a fluidizing manner similar to Example 1 where propylene was dimerized with various nickel complexes with diethylaluminum chloride (DEAC). The gaseous hourly space velocity of propylene was about 1000. The ratio of aluminum compound to nickel complex is 10:1. The runs were conducted under atmospheric pressure at autogenous temperatures. The solid support was silica-alumina in all cases. The results are given in Table VII.

EXAMPLE VIII

In a manner analogous to that of the preceding examples, ethylene and propylene were codimerized with various nickel complex-containing catalyst systems. The reactions were carried out in a 1400 ml stirred tank with n-pentane as solvent. A measured weight of propylene was added and the temperature was adjusted to 80° F. Ethylene was then added at 5 to 10 psi partial pressure followed by addition of the dry solid portion of the catalyst. This solid was prepared either by addition of the nickel complex in dry pentane solution to the preactivated support (a silica gel having a water slurry pH of about 3.3) or by addition of a dry solution of the nickel salt followed by addition of the complexing ligand. Diethylaluminum chloride was added at a 6:1 molar ratio of aluminum to nickel.

The runs varied in length from 1.5 to 4 hours, the rate data being taken after the first one-half to one hour of

TABLE VII

| Run | Nickel Complex | Time Hrs. | Temp. °F. | Conv. % | Selectivity to hexenes % | Distribution of Hexene Isomeric Structures[b] | | |
|---|---|---|---|---|---|---|---|---|
| | | | | | | 2,3-Dimethyl-butane | 2-methyl-pentane | n-hexane |
| 1 | (3-picoline)₂NiCl₂ | 2.5 | 121 | 11.7 | 87.3 | 5.7 | 68.0 | 26.3 |
| 2 | (4-picoline)₂NiCl₂ | 2.5 | 98 | 12 | 88 | 4.6 | 69.2 | 25.7 |
| 3 | (4-ethylpyridine)₂NiCl₂ | 3.0 | 85 | 24 | 69 | 4.7 | 67.2 | 28.0 |
| 4 | (3-picoline)₂NiCl₂[a] | 2.5 | 84 | <5 | — | 21.7 | 65.0 | 13.3 |
| 5 | (2-picoline oxide)₂NiCl₂ | 2.5 | 122 | 36 | 42 | 6.0 | 68.5 | 25.4 |

[a]No organoaluminum compound was employed in this run.
[b]Determined on hydrogenated sample.

These runs demonstrate that a monoolefin such as propylene can be dimerized with various nickel complexes on solid supports, either alone or with an organoaluminum compound.

operation. The catalyst systems still showed activity after 4 hours.

The results of these runs are shown in Table VIII.

TABLE VIII

Codimerization of Ethylene-Propylene Using Silica-Supported Nickel Salt Complexed With Various Phosphine Ligands

| Phosphine | Tri-n-butyl | Tri-n-octyl | Triphenyl | Tricyclohexyl | Triisopropyl[a] |
|---|---|---|---|---|---|
| Rate of Formation g/g complex/hr. | | | | | |
| C₄ olefin | 1700 | 560 | 3200 | 1000 | 205 |
| C₅ olefin | 5700 | — | 2000 | 550 | 275 |
| C₆ olefin | 4000 | 160 | 300 | 450 | 355 |
| C₇+ olefin | — | — | — | — | 35 |
| Total | 11400 | 720 | 5500 | 2000 | 870 |
| Selectivity of: | | | | | |
| Ethylene to C₅ olefin | 50 | — | 20 | 16 | 35 |
| Propylene to C₅ olefin | 49 | — | 80 | 38 | 32 |
| Normal olefin, % of C₅ | 38 | — | 43 | 50 | 27 |
| C₆ Olefin composition, % | | | | | |
| n-C₆ | 16 | 20 | 20 | 45 | 10 |
| 2-methylpentenes | 65 | 66 | 65 | 44 | 48 |

TABLE VIII-continued

Codimerization of Ethylene-Propylene Using Silica-Supported Nickel Salt Complexed With Various Phosphine Ligands

| Phosphine | Tri-n-butyl | Tri-n-octyl | Triphenyl | Tricyclohexyl | Triisopropyl[a] |
|---|---|---|---|---|---|
| 2,3-dimethylbutenes | 19 | 14 | 15 | 13 | 42 |

[a]On silica-alumina

We claim:

1. A process for dimerizing at least one monoolefin selected from the group consisting of ethylene and propylene which comprises contacting said monoolefin with a catalyst under suitable reaction conditions, said catalyst having been prepared by:
   A. heat treating a solid catalyst support consisting essentially of silica, silica-alumina, or mixtures thereof, with flowing air at a temperature in the range of 800° to 1500°F. for a time in the range of 0.1 to 24 hours, said solid catalyst support being characterized by a pH value of less than 6 when slurried with distilled and decarbonated water, and
   B. contacting the thus heat treated solid catalyst support with (a) a nickel complex selected from the group consisting of componds having the formula

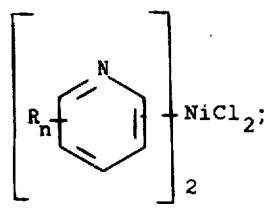

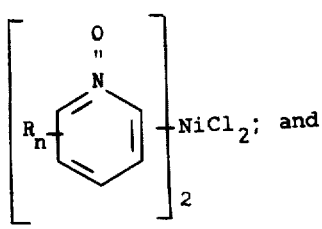

$(R_3P)_2NiCl_2$, wherein each R is individually selected from alkyl radicals having up to 20 carbon atoms; and n is zero or an integer in the range of 1 to 5; and (b) an aluminum compound having the formula $R_xAlCl_y$, wherein R is as previously defined, and $x$ and $y$ are integers in the range of 0 to 3 with the sum of $x$ and $y$ being 3.

2. A process in accordance with claim 1 wherein each of $x$ and $y$ has a value of at least 1.

3. A process in accordance with claim 2 wherein said support is silica-alumina.

4. A process in accordance with claim 1 wherein said pH value is less than 4.

5. A process in accordance with claim 4 wherein said nickel complex is selected from the group consisting of bis(2-picoline oxide)dichloronickel, bis(3-picoline)dichloronickel, bis(4-picoline)dichloronickel, bis(4-ethylpyridine)dichloronickel, and bis(tri-n-butylphosphine)dichloronickel.

6. A process in accordance with claim 1 wherein said support is silica.

7. A process in accordance with claim 5 wherein said aluminum compound is diethyl aluminum chloride, ethyl aluminum dichloride, or triethyl aluminum.

8. A process in accordance with claim 7 wherein said nickel complex is bis(tri-n-butylphosphine)dichloronickel, said support is silica, and said aluminum compound is diethyl aluminum chloride.

9. A process in accordance with claim 1 wherein said nickel complex is bis(tri-n-butylphosphine)dichloronickel, said support is silica-alumina, and said aluminum compound is diethyl aluminum chloride.

10. A process in accordance with claim 1 wherein said nickel complex is bis(tri-n-butylphosphine)dichloronickel.

11. A process in accordance with claim 8 wherein said monoolefin is ethylene.

12. A process in accordance with claim 8 wherein said monoolefin is propylene.

13. A process in accordance with claim 1 wherein said nickel compound is

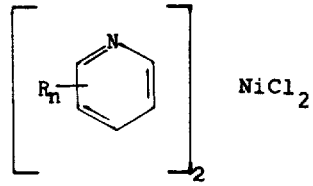

14. A process in accordance with claim 1 wherein said nickel compound is

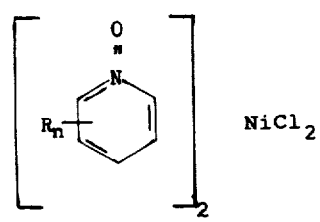

15. A process in accordance with claim 1 wherein said nickel compound is $(R_3P)_2NiCl_2$.

16. A process in accordance with claim 1 wherein said reaction conditions comprise temperatures in the range of from −50° to 225°F., a pressure in the range of 20 to 500 psig, a reaction time in the range of from about 0.1 minute to about 20 hours, the mole ratio of said aluminum compound to said nickel complex ranges from 0.1:1 to 20:1, and the mole ratio of said nickel complex to said monoolefins ranges from about 0.00001 to about 0.1:1.

* * * * *